United States Patent

Padia et al.

[11] Patent Number: 5,958,950
[45] Date of Patent: Sep. 28, 1999

[54] BENZIMIDAZOLE COMPOUNDS USEFUL FOR THE TREATMENT OF INFLAMMATORY DISEASE, ATHEROSCLEROSIS, RESTENOSIS OR INHIBITING LIPOXYGENASE

[75] Inventors: Janak Khimchand Padia, Ypsilanti; Bruce David Roth, Plymouth; Bharat Kalidas Trivedi, Farmington Hills, all of Mich.

[73] Assignee: Warner-Lambert Company, Morris Plains, N.J.

[21] Appl. No.: 09/011,227

[22] PCT Filed: Oct. 2, 1996

[86] PCT No.: PCT/US96/15857

§ 371 Date: Feb. 5, 1998

§ 102(e) Date: Feb. 5, 1998

[87] PCT Pub. No.: WO97/12615

PCT Pub. Date: Apr. 10, 1997

Related U.S. Application Data

[60] Provisional application No. 60/005,201, Oct. 5, 1995.

[51] Int. Cl.$^6$ ...................... A61K 31/425; A61K 31/445; A61K 31/44
[52] U.S. Cl. .................... 514/321; 514/326; 514/340; 514/341; 514/365; 546/199; 546/269.7; 546/273.4; 548/181; 548/201
[58] Field of Search .................... 548/181; 514/365, 514/340, 341, 321, 326; 546/199, 269.7, 273.4

[56] References Cited

U.S. PATENT DOCUMENTS

| | | | |
|---|---|---|---|
| 3,183,239 | 5/1965 | Brown | 548/181 X |
| 3,299,080 | 1/1967 | Gal et al. | 548/181 |
| 3,325,506 | 6/1967 | Jones et al. | 548/181 X |
| 3,326,753 | 6/1967 | Brown et al. | 548/181 X |
| 3,481,947 | 12/1969 | Ennis | 548/181 |
| 3,535,331 | 10/1970 | Brown et al. | 548/181 X |
| 3,538,108 | 11/1970 | Pines | 548/181 |
| 3,590,047 | 6/1971 | Shen et al. | 260/309.2 |
| 3,658,827 | 4/1972 | Bezou | 548/181 |
| 3,899,503 | 8/1975 | Alaimo et al. | 548/181 |
| 5,032,588 | 7/1991 | Brooks et al. | 514/224.8 |

FOREIGN PATENT DOCUMENTS

| | | | |
|---|---|---|---|
| 0260229 | 6/1965 | Australia | 548/181 |
| 0672520 | 5/1964 | Belgium | 548/181 |
| 0240026 | 10/1987 | European Pat. Off. . | |
| 0419210 | 3/1991 | European Pat. Off. . | |
| 0258814 | 8/1988 | Germany | 548/181 |
| 0261153 | 10/1988 | Germany | 548/181 |
| 1191039 | 5/1970 | United Kingdom | 548/181 |
| 9009801 | 9/1980 | WIPO . | |
| 9108744 | 6/1991 | WIPO . | |

OTHER PUBLICATIONS

Bukowski, Aeta Pol. Pharm., vol. 36, (06), pp. 651–656, 1977.
Kuwubara et al, Chemical Abstracts, vol. 84 (25), # 175142, Jan. 8, 1976.
Nishi et al, Chemical Abstracts, vol. 114 (21), # 207259, Dec. 20, 1990.
Strehlke et al, Chim. Ther., vol. 8 (5), pp. 571–573, 1973.
Suzuki et al, Agr. Biol. Chem., vol 36 (12) pp. 2213–2221, 1972.
Berndt, et al., "Some Reactions of 2–Benzimidazolecarbonitrile", *Notes*, vol. 9, 1972, 137–140.

*Primary Examiner*—Floyd D. Higel
*Attorney, Agent, or Firm*—Elizabeth M. Anderson

[57] ABSTRACT

A method for the treatment of inflammatory disease or condition atherosclerosis or restenosis or for inhibiting 15 lipaxygenase in a mammal in need thereof comprising administering to such mammal an effect amount of a compound of Formula I

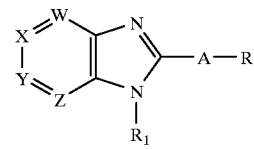

22 Claims, No Drawings

BENZIMIDAZOLE COMPOUNDS USEFUL FOR THE TREATMENT OF INFLAMMATORY DISEASE, ATHEROSCLEROSIS, RESTENOSIS OR INHIBITING LIPOXYGENASE

This application claims the benefit of U.S provisional application 60/005,201, filed Oct. 5, 1995. This application is filed in accordance with 35 U.S.C. §371 from PCT/US96/15857, filed Oct. 2, 1.996.

FIELD OF THE INVENTION

The present invention relates to novel compounds and medical methods of treatment of inflammation, atherosclerosis and restenosis. More particularly, the present invention concerns the use of novel benzimidazole derivatives.

BACKGROUND OF THE INVENTION

Lipoxygenases are nonheme iron-containing enzymes that catalyze the oxygenation of certain polyunsaturated fatty acids such as lipoproteins. Several different lipoxygenase enzymes are known, each having a characteristic oxidation action. One specific lipoxygenase, namely 15-LO, has been detected in atherosclerotic lesions in mammals, specifically rabbit and man. The enzyme, in addition to its role in oxidative modification of lipoproteins, is important in the inflammatory reaction in the atherosclerotic lesion. Indeed, 15-LO has been shown to be induced in human monocytes by the cytokine IL-4, which is known to be implicated in the inflammatory process.

We have now found that inhibitors of 15-LO are especially useful to prevent and treat inflammation and atherosclerosis. While there are several lipoxygenase enzymes, specific inhibition of 15-LO is important in the inflammatory and atherosclerosis process. All that is required according to this invention is to administer a 15-LO inhibitor, and especially one that is a specific 15-LO inhibitor.

SUMMARY OF THE INVENTION

Accordingly, a first embodiment of the present invention provides a method of treatment of chronic or acute inflammatory disease, atherosclerosis and restenosis in mammals in need thereof comprising administering to such mammal an effective amount of a benzimidazole of Formula I or a pharmaceutically acceptable salt thereof:

FORMULA I

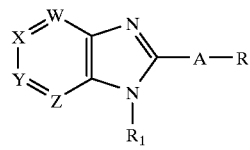

where W, X, Y and Z can be independently C-$R_2$, C—$R_3$, C—$R_4$, C—$R_5$, or N;
$R_2$, $R_3$, $R_4$ and $R_5$ can be independently
H,
$C_{1-20}$ alkyl,
halogen,
CN,
nitro,
—$SO_2H$,
—$SO_2$ lower alkyl of from 1–4 carbon atoms,
—$SO_2NR_6R_7$,
alkoxy of from 1–4 carbon atoms;
—SH,
—$(CH_2)_nNR_6R_7$,
—$N(R_6)C(O)NR_7R_8$,
—$N(R_6)C(S)NR_7R_8$,
—$N(R_6)(CH_2)_nNR_7R_8$
—$(CH_2)_nCONR_6R_7$,
—$(CH_2)_nOR_6$,
—$(CH_2)_nCO_2R_6$,
—$(CH_2)_nOC(O)R_6$, or
—$CF_3$;
n is an integer of from 0 to 4;
$R_1$ can be H or lower alkyl of from 1–4 carbon atoms;
A is a 5 or 6 member heterocyclic ring containing at least one of N, O, or S which is substituted by
R and may be substituted by $R_{12}$ wherein;
R and $R_{12}$ can be independently $R_2$ as described above, cycloalkyl of from 5 to 12 carbon atoms or bicyclic ring structure of from 6 to 12 atoms, either with up to 3 substitutents as $R_2$, mono or polyaryl of from 6 to 10 carbon atoms with up to 3 substitutents as $R_2$, mono or polyheterocyclic of from 5 to 10 atoms having at least one N, O or S atom and up to 3 substitutents as $R_2$,
additionally, R and $R_{12}$ when taken together can form a mono- or bicyclic ring of from 4 to 10 carbon atoms which may be substituted by $R_4$ or $R_5$ or an amino group;
$R_6$, $R_7$ and $R_8$ can also be independently hydrogen, saturated (1–12 carbon atoms) or unsaturated (2–12 carbon atoms) hydrocarbon with terminal functionality of —$NR_9R_{10}$ or nitrogen heterocycle of from 5 to 7 atoms or piperidine with nitrogen or oxygen in position 4 on the ring;
$R_9$ and $R_{10}$ can be independently H, alkyl of from 1–4 carbon atoms or benzyl; or
a pharmaceutically acceptable salt thereof.

A still further and second embodiment of the present invention is a method of treatment of atherosclerosis in mammals in need thereof comprising administering to such mammal an effective amount of a compound selected from the group consisting of: a compound of formula I in combination with one or more agents selected from the group consisting of:
(a) ACAT inhibitor;
(b) HMG-COA reductase inhibitor;
(c) Lipid regulator; and
(d) Bile acid sequestrant;
or a pharmaceutically acceptable salt thereof.

Also, the invention is directed to the novel compositions of Formula I.

Finally, the present invention is directed to a pharmaceutical composition for administering an effective amount of a compound of Formula I in unit dosage form in the treatment methods mentioned above.

DETAILED DESCRIPTION OF THE INVENTION

In the compounds of Formula I, the term "lower alkyl" means a straight or branched hydrocarbon radical having from 1 to 4 carbon atoms and includes, for example, methyl, ethyl, n-propyl, isopropyl, n-butyl, sec-butyl, isobutyl or tert-butyl.

The term "lower alkoxy" is O-alkyl as defined above for alkyl. "Halogen" is fluorine, chlorine, bromine, or iodine.

Heterocycle is defined as five or six-membered mono, bicyclic or fused ring structures which may contain one or more heteroatom such as N, O or S; examples of heterocycle are pyridine, thiophene, pyrimidine, pyridazine, pyrazole, thiazole, oxazole, indole, N-alkylindole, quinoline, quinazoline, quinazolinone, piperidine, morpholine, piperazine, pyrrolidine and the like. Substitutents can be hydrogen, alkyl of from 1–4 carbon atoms; cycloalkyl of from 5–7 carbon atoms, $SR_6$, $(CH_2)_n$—$NR_6R_7$, CN, —$COOR_6$, —$(CH)_nOR_6$, —$CONR_6R_7$, —$COR_6$, —$(CH)_n CONR_6R_7$, $SO_2NR_6R_7$, $NHCOR_6$, $NR_6 CONR_7$ where $R_6$, $R_7$ and n are as defined above.

Some preferred heterocyclic materials for A are shown in Formula II where the benzimidazole ring structure and the R substitutent thereto can be on either position on the heterocyclic ring as shown by the bonds from the rings;

FORMULA II

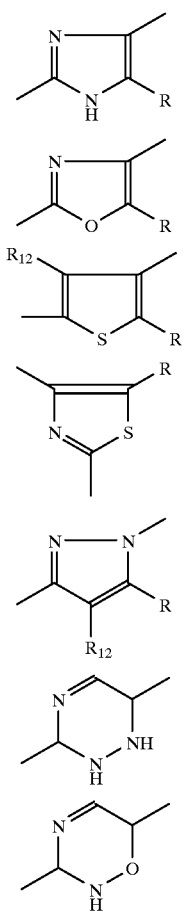

The term "mammal" includes animals and humans.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and bicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. Pharma. Sci.*, 1977;66:1).

The acid addition salts of said basic compounds can be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts can be formed with metals or amines, such as alkali and alkaline earth metals or organic amines. Examples of such metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, Supra, 1977).

The base addition salts of said acidic compounds can be prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of the first embodiment used in the method of the present invention is a compound formula I of:

FORMULA I

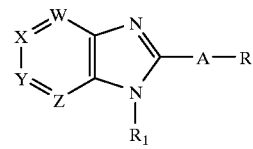

where W, X, Y and Z can be independently $C-R_2$, $C-R_3$, $C-R_4$, $C-R_5$ or N;

$R_2$, $R_3$, $R_4$ and $R_5$ can be independently
H,
$C_{1-20}$ alkyl,
halogen,
CN,
nitro,
—$SO_2H$,
—$SO_2$ lower alkyl of from 1–4 carbon atoms,
—$SO_2NR_6R_7$,
alkoxy of from 1–4 carbon atoms;
—SH,
—$(CH_2)_nNR_6R_7$,
—$N(R_6)C(O)NR_7R_8$,
—$N(R_6)C(S)NR_7R_8$,
—$N(R_6) (CH_2)_nNR_7R_8$
—$(CH_2)_nCONR_6R_7$,
—$(CH_2)_nOR_6$,
—$(CH_2)_nCO_2R_6$,
—$(CH_2)_nOC(O)R_6$, or
—$CF_3$;

n is an integer of from 0 to 4;
$R_1$ can be H or lower alkyl of from 1–4 carbon atoms;
A is a 5 or 6 member heterocyclic ring containing at least one of N, O, or S which is substituted by
R and may be substituted by $R_{12}$ wherein;
  R and $R_{12}$ can be independently $R_2$ as described above, cycloalkyl of from 5 to 12 carbon atoms or bicyclic ring structure of from 6 to 12 atoms, either with up to 3 substitutents as $R_2$, mono or polyaryl of from 6 to 10 carbon atoms with up to 3 substitutents as $R_2$, mono or polyheterocyclic of from 5 to 10 atoms having at least one N, O or S atom and up to 3 substitutents as $R_2$,
additionally, R and $R_{12}$ when taken together can form
  a mono- or bicyclic ring of from 4 to 10 carbon atoms which may be substituted by $R_4$ or $R_5$ or an amino group;
$R_6$, $R_7$ and $R_8$ can also be independently hydrogen, saturated (1–12 carbon atoms) or unsaturated (2–12 carbon atoms) hydrocarbon with terminal functionality of —$NR_9R_{10}$ or nitrogen heterocycle of from 5 to 7 atoms or piperidine with nitrogen or oxygen in position 4 on the ring; $R_9$ and $R_{10}$ can be independently H, alkyl of from 1–4 carbon atoms or benzyl; or
a pharmaceutically acceptable salt thereof.

Examples of preferred benzimidazoles are Formula III as follows:

FORMULA III

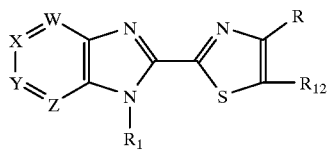

where W, X, Y, Z, R, $R_1$ and $R_{12}$ are as described above.

Some preferred compounds of Formula III are where R is a substituted phenyl group, especially when $R_{12}$ is hydrogen or halogen.

Some additional preferred compounds of Formula III are where any one of W, X, Y or Z is nitrogen.

A benzimidazole compound can be administered to a mammal (e.g., a human) alone or in conjunction with (before, along with or subsequent to) one or more other benzimidazole compounds or another agent to be administered.

Preferred compounds used in the second embodiment of the present invention include one or more agents selected from the group consisting of an acyl CoA:cholesterol acyltransferase (ACAT) inhibitor; 3-hydroxy-3-methylglutaryl-coenzyme A reductase (HMG-COA reductase) inhibitor; lipid regulator; and bile acid sequestrant.

Examples of ACAT inhibitors include DL-melinamide disclosed in British Patent 1,123,004 and Japan. J. Pharmacol., 1986;42:517–523; 2,2-dimethyl-N-(2,4,6-trimethoxyphenyl)dodecanamide disclosed in U.S. Pat. No. 4,716,175; N-[2,6-bis(1-methylethyl)phenyl]-N'-[[1-(4-dimethylaminophenyl)cyclopentyl]methyl]urea disclosed in U.S. Pat. No. 5,015,644; 2,6-bis(1-methylethyl)phenyl[[2,4,6-tris(1-methylethyl)phenyl]acetyl]sulfamate disclosed in copending U.S. patent application Ser. No. 08/233,932 filed Apr. 13, 1994; and the like. U.S. Pat. Nos. 4,716,175 and 5,015,644 and U.S. patent application Ser. No. 08/233,932 and British Patent 1,123,004 and Japan. J. Pharmacol., 1986;42:517–523 are hereby incorporated by reference.

Examples of HMG-COA reductase inhibitors include lovastatin disclosed in U.S. Pat. No. 4,231,938; pravastatin disclosed in U.S. Pat. No. 4,346,227; simvastatin disclosed in U.S. Pat. No. 4,444,784; fluvastatin disclosed in U.S. Pat. No. 4,739,073; atorvastatin disclosed in U.S. Pat. Nos. 4,681,893 and 5,273,995; and the like. U.S. Pat. Nos. 4,231,938; 4,346,227; 4,444,784; 4,681,893; 4,739,073 and 5,273,995 are hereby incorporated by reference.

Examples of bile acid sequestrants include colestipol disclosed in U.S. Pat. Nos. 3,692,895 and 3,803,237; cholestyramine disclosed in U.S. Pat. No. 3,383,281 and Casdorph R. in Lipid Pharmacology., 1976;2;222–256, Paoletti C., Glueck J., eds. Academic Press, New York; and the like. U.S. Pat. Nos. 3,692,895; 3,803,237 and 3,383,281 and R. Casdorph, supra, 1976, are hereby incorporated by reference.

Examples of lipid regulators include gemfibrozil described in U.S. Pat. No. 3,674,836; bezafibrate disclosed in U.S. Pat. No. 3,781,328; clofibrate disclosed in U.S. Pat. No. 3,262,850; fenofibrate disclosed in U.S. Pat. No. 4,058,552; niacin disclosed in McElvain, et al., Org. Syn., 1925;4:49; and the like. U.S. Pat. Nos. 3,674,836; 3,781,328; 3,262,850 and 4,058,552 and McElvain, et al., Org. Syn., 1925;4:49 are hereby incorporated by reference.

Methods of preparing ACAT inhibitors, HMG-CoA reductase inhibitors, lipid regulators, and bile acid sequestrants used in the second embodiment of the present invention are disclosed in the aforementioned references.

The invention is also concerned with compounds as benzimidazole derivatives:

A compound of formula I

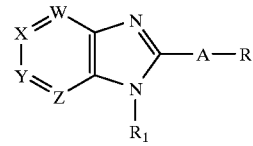

where W, X, Y and Z can be independently C—$R_2$, C—$R_3$, C—$R_4$, C—$R_5$ or N;
$R_2$, $R_3$, $R_4$ and $R_5$ can be independently
H,
$C_{1-20}$ alkyl,
halogen,
CN,
nitro,
—$SO_2H$, —SO$_2$ lower alkyl of from 1–4 carbon atoms,
—SO$_2$NR$_6$R$_7$,
alkoxy of from 1–4 carbon atoms;
SH,
—(CH$_2$) NR$_6$R$_7$,
—N(R$_6$)C(O)NR$_7$R8,
—N(R$_6$)C(S)NR$_7$R$_8$,
—N(R$_6$) (CH$_2$)$_n$NR$_7$R$_8$
—(CH$_2$)$_n$CONR$_6$R$_7$,
—(CH$_2$)$_n$OR$_6$,
—(CH$_2$)$_n$CO$_2$R$_6$,
—(CH$_2$)$_n$OC(O)R$_6$, or
—CF$_3$;
n is an integer of from 0 to 4;
R$_1$ can be H or lower alkyl of from 1–4 carbon atoms;
A is a 5 or 6 member heterocyclic ring containing at least one of N, O, or S which is substituted by R and may be substituted by R$_{12}$ wherein;
R and R$_{12}$ can be independently R$_2$ as described above, cycloalkyl of from 5 to 12 carbon atoms or bicyclic ring structure of from 6 to 12 atoms, either with up to 3 substitutents as R$_2$, mono or polyaryl of from 6 to 10 carbon atoms with up to 3 substitutents as R$_2$, mono or polyheterocyclic of from 5 to 10 atoms having at least one N, O or S atom and up to 3 substitutents as R$_2$, additionally, R and R$_{12}$ when taken together can form a mono- or bicyclic ring of from 4 to 10 carbon atoms which may be substituted by R$_4$ or R$_5$ or an amino group;
R$_6$, R$_7$ and R$_8$ can also be independently hydrogen, saturated (1–12 carbon atoms) or unsaturated (2–12 carbon atoms) hydrocarbon with terminal functionality of —NR$_9$R$_{10}$ or nitrogen heterocycle of from 5 to 7 atoms or piperidine with nitrogen or oxygen in position 4 on the ring; R$_9$ and R$_{10}$ can be independently H, alkyl of from 1–4 carbon atoms or benzyl;
provided that when W, X, Y and Z are —CH—, R$_1$ is H and A is thiazole attached to the benzimidazole ring at the 2-position of the thiazole ring (a) the position alpha to the nitrogen in the thiazole ring is not substituted by an oxygen when position alpha to the sulfur is phenyl and (b) when the position alpha to the sulfur is hydrogen, the position alpha to the nitrogen may not be phenyl, 4-chlorophenyl, 4-fluorophenyl, 4-nitrophenyl, 2,5-dichlorophenyl, 2-furanyl, 2-thienyl, 3-pyridine or 2-pyridine; or a pharmaceutically acceptable salt thereof.

General Synthesis:

Compounds of Formula I can be synthesized as follows. The following is a known compound.

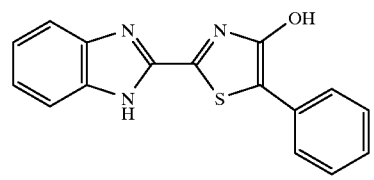

SCHEME A

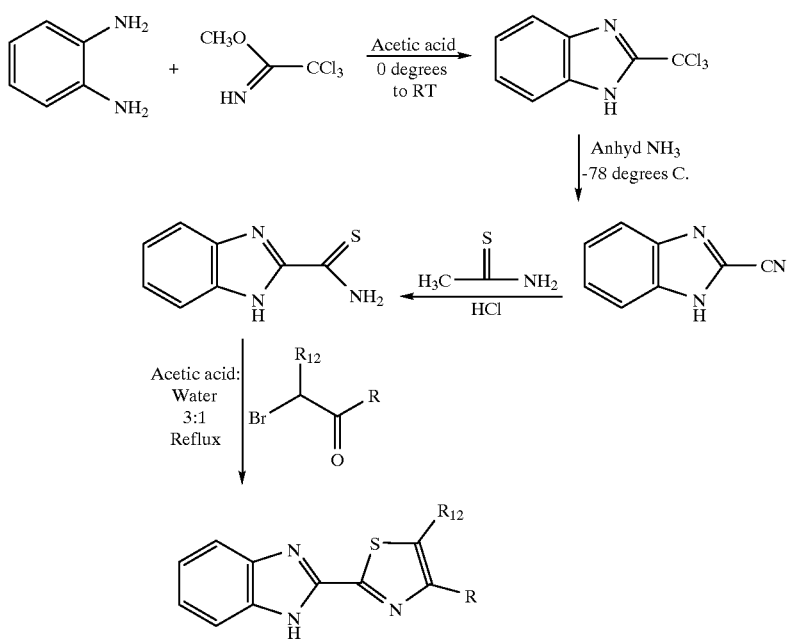

SCHEME B

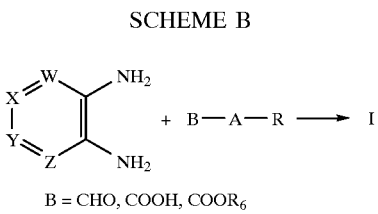

B = CHO, COOH, COOR$_6$

The compounds of Formula I can be prepared as shown in Scheme A.

The required 2-trichloromethylbenzimidazole can be obtained by the reaction of the corresponding diamine and the trichloroacetimidate at 0° C. to room temperature in an organic solvent (Holan, G. et al., J. Chem. Soc. (C), (1967), Page 20). The reaction of 2-trichloromethylbenzimidazole with anhydrous ammonia or ammonium hydroxide can provide the corresponding carbonitrile derivative, (Holan, G. et al., J. Chem. Soc. (C), (1967), Page 25). The reaction of the carbonitrile derivative with thioacetamide in an organic solvent like DMF in presence of dry hydrogen chloride can provide the thiocarboxamide derivative. Condensation of the thiocarboxamide with the required a haloketone or a haloaldehyde or haloester in a solvent or a mixture of solvents such as acetic acid, water, DMF, THF, dioxane, toluene, methanol, and ethanol preferably in acetic acid-water can provide the desired compounds of Formula I. The condensation can be carried out at room temperature —150° C. preferably at a reflux temperature. (Berndt, E. W. et al., J. of Heterocycle Chem., Year 1972, Volume 9, Page 137–140.)

The compounds of formula I can also be prepared by condensation of required diamine with the corresponding derivative of Formula IV as shown in Scheme B (Benzimidazoles and Congeneric Tricyclic Compounds, Editor: Preston, P. N. et al., Publisher: John Wiley & Sons).

The benzimidazoles are valuable agents for the treatment of inflammatory diseases or conditions, atherosclerosis and restenosis.

15-Lipoxygenase Assay

The 15-LO inhibitors are effective for treating inflammation and atherosclerosis. A characteristic feature of atherosclerosis is the accumulation of cholesterol ester engorged from foam cells. Foam cells are derived from circulating monocytes which invade artery walls in response to hypercholesterolemia, and mature into tissue macrophages. The enzyme 15-LO has been implicated in flammatory disorders and in the origin and recruitment of foam cells (see Harats, et al., *Trends Cardioivasc. Med.*, 1995;5(1):29–36). This enzyme is capable of oxidizing esterifieid polyenoic fatty acids, such as those found in phospholipids. Treatment of experimental animals with antioxidants which reduce hydroperoxides produced by 15-LO has been shown to retard the progression of atherosclerotic lesions. Accordingly, administering compounds which inhibit 15-LO is an effective way to treat and prevent atherosclerosis.

The compounds described above are effective inhibitors of 15-LO when evaluated in standard assays routinely utilized to measure 15-LO activity. Specifically, representative compounds were evaluated by the methods described by Auerbach, et al., *Analytical Biochemistry*, 1992; 201:375–380. Two in vitro assays were utilized, both utilizing rabbit reticulocyte 15-LO, and linoleic acid as substrate, to enzymatically produce a peroxide oxidation product known as 13(S)-HPODE. N-Benzoyl leucomethylene blue was utilized as a calorimetric reagent for detection and quantification of the peroxide formation. Also, HPLC was utilized to quantify the oxidation following incubation at 4° C. for 10 minutes.

The 15-LO inhibitory activity of representative compounds is presented in Table I. The data column gives the concentration of compounds required to inhibit 50% of the activity of 15-LO ($IC_{50}$) when measured by the HPLC method of Auerbach, et al.

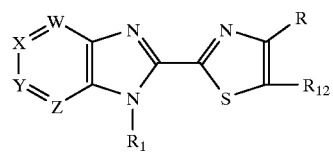

Wherein W, X, Y and Z are C—H and $R_1$ is hydrogen.

TABLE I

| Example | R | $R_{12}$ | $IC_{50} \mu M$ |
|---|---|---|---|
| 1 | 2-pyridyl | H | 0.36 |
| 2 | 4-Cl—Ph | H | 0.62 |
| 3 | 4-F—Ph | H | 0.189 |
| 5 | 2,5-$Cl_2$ | H | 0.207 |
| 6 | Ph | H | 0.115 |
| 7 | 2-thienyl | H | 0.096 |
| 8 | 3-MeO—Ph | H | 0.5 |
| 9 | 2-MeO—Ph | H | 0.125 |
| 10 | 4-MeO—Ph | H | 1.65 |
| 11 | 4-Ph—Ph | H | >10 $\mu M$ |
| 12 | 4-OH—Ph | H | >2.5 |
| 13 | 3,4(OH)$_2$—Ph | H | >2.5 |
| 14 | 5-Br,2-OH—Ph | H | 91.3% @ 10 $\mu M$ |
| 15 | 2,5-(MeO)$_2$—Ph | H | 0.39 |
| 16 | 2,6(MeO)$_2$—Ph | H | >10 $\mu M$ |
| 17 | 2-OH—Ph | H | 0.04(P), 0.08(Q) |
| 18 | 4-Me—Ph | H | 71.6% @ 10 $\mu M$ |
| 19 | 2-Me—Ph | H | 0.33 |
| 20 | 3-Cl—Ph | H | 0.2 |
| 21 | 4-Br—Ph | H | 0.46 |
| 22 | 2,4-$Cl_2$—Ph | H | — |
| 23 | 2-$NO_2$—Ph | H | — |
| 24 | 3-$NO_2$—Ph | H | — |
| 25 | $CH_2$NPhth | H | >10 $\mu M$ |
| 26 | H | Ph | — |
| 27 | Ph | Br | 0.773 |
| 28 | Ph | COOEt | 69% @ 10 $\mu M$ |
| 29 | Ph | COOH | >10 $\mu M$ |
| 30 | COOEt | H | 25% @ 10 $\mu M$ |
| 31 | COOH | H | 1.38% @ 10 $\mu M$ |
| 32 | CO(CH$_2$)$_3$—N(piperidine) | H | >10 $\mu M$ |
| 33 | CONHPh | H | 25.1% @ 10 $\mu M$ |
| 34 | Ph | NHCOOBz | 89.25% @ 10 $\mu M$ |
| 35 | 3-CN—Ph | H | 45% @ 10 $\mu M$ |
| 36 | OH | Ph | >10 $\mu M$ |
| 37 | 4-Pyridyl | H | 0.54(P), 0.81(Q) |

The compounds of the present invention can be prepared and administered in a wide variety of routes of administration such as parenteral, oral, topical, rectal, inhalation and the like. Formulations will vary according to the route of administration selected. Examples are oral and parenteral dosage forms. Thus, the compounds of the present invention can be administered by injection, that is, intravenously, intramuscularly, intra-cutaneously, subcutaneously, intraduodenally, or intra-peritoneally. Also, the compounds of the present invention can be administered by inhalation, for example, intranasally. Additionally, the compounds of the present invention can be administered transdermally. The following dosage forms may comprise as the active component, a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted for example from about 0.1 mg to 200 mg, preferably about 0.5 mg to loo mg according to the particular application and the potency of the active component. The composition can, if desired, also contain other compatible therapeutic agents.

In therapeutic use as agents for the treatment of inflammatory diseases, atherosclerosis and restenosis, the compounds utilized in the pharmaceutical methods of this invention can be administered at an initial dosage of about 0.01 mg to about 200 mg/kg daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The ACAT inhibitors, HMG-CoA reductase inhibitors, lipid regulators, and bile acid sequestrants utilized in the second embodiment of the present invention can be used in standard dosage amounts known in the art.

As further exemplification of the invention listed below are preferred embodiments wherein all parts are parts by weight and all temperatures are degrees Centigrade unless otherwise indicated.

EXAMPLES

Example 8

2-[4-(3-Methoxy-phenyl)-thiazol-2-yl]-1H-benzoimidazole

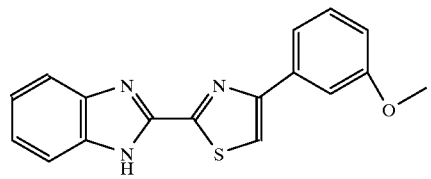

A solution of 1H-Benzoimidazole-2-carbothioic acid amide (0.885 g, 5 mmol) and 3-methoxyphenacylbromide (1.15 g, 5.05 mmol) in 3:1 acetic acid-water (25 ml) was refluxed for 1 hour. The reaction mixture was cooled to room temperature and solid was collected. The solid was treated with aqueous ammonium hydroxide. This slurry obtained was heated and filtered while it was hot. The solid was washed with water. Crystallization from ethyl alcohol yielded 0.75 gm (49%) of the title compound as off white crystals. mp 157–158° C.

Example 9
2-[4-(2-Methoxy-phenyl)-thiazol-2-yl]-1H-benzoimidazole

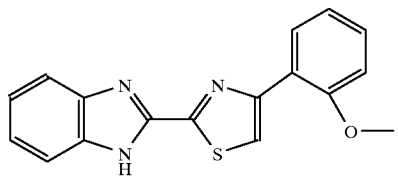

The titled compound was prepared by the method as described for example-8, but using 2-methoxyphenacylbromide. The titled compound was isolated as a light-yellow solid (0.85 g, 27.68%) mp 209–210° C.

Example 10
2-[4-(4-Methoxy-phenyl)-thiazol-2-yl]-1H-benzoimidazole

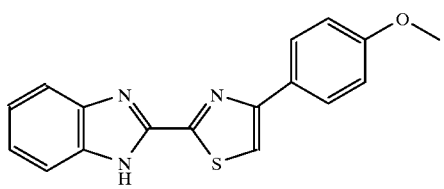

The titled compound was prepared by the method as described for Example 8, but using 4-methhoxyphenacylbromide. The titled compound was isolated as a light-yellow solid (1.03 g, 67%) mp 243–245° C.

Example 11
2-(4-Biphenyl-4-yl-thiazol-2-yl)-1H-benzoimidazole

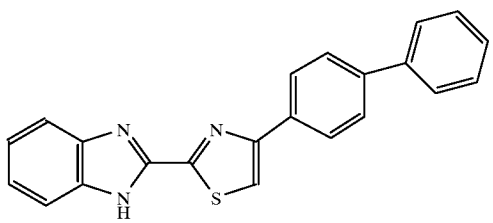

The titled compound was prepared by the method as described for Example 8, but using 4-phenylphenacylbromide. The titled compund was isolated as a light-yellow solid (0.72 g, 20.4%) mp>270° C.

Example 12
4-[2-(1H-Benzoimidazol-2-yl)-thiazol-4-yl]-phenol

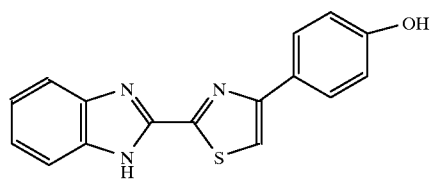

The titled compound was prepared by the method as described for Example 8, but using 4-hydroxyphenacylbromide. The titled compound was isolated as a dark gray solid (0.55 g, 37.5%) mp 251–252° C.

Example 13
4-[2-(1H-Benzoimidazol-2-yl)-thiazol-4-yl]-benzene-1,2-diol

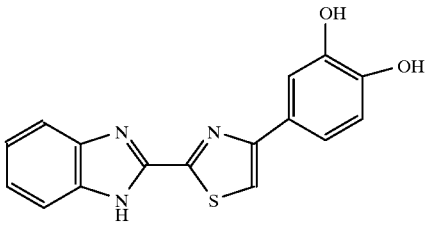

The titled compound was prepared by the method as described for Example 8, but using 3,4-dihydroxyphenacylbromide. The titled compound was isolated as a dark olive solid (0.45 g, 29%) mp 173–177° C. (decomp.).

Example 14
2-[2-(1H-Benzoimidazol-2-yl)-thiazol-4-yl]-4-bromo-phenol

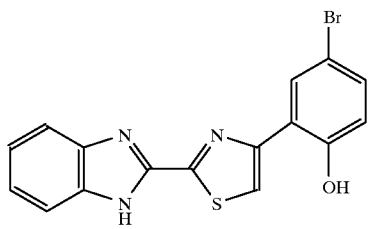

The titled compound was prepared by the method as described for Example 8, but using 5-bromo-2-hydroxyphenacylbromide. The titled compound was isolated as a white solid (0.33 g, 44.3%) mp 280–282° C.

Example 15
2-[4-(2,5-Dimethoxy-phenyl)-thiazol-2-yl]-1H-benzoimidazole

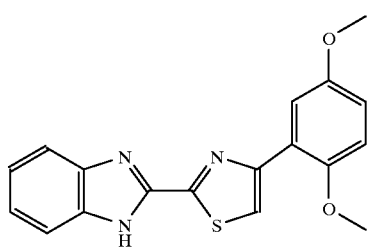

The titled compound was prepared by the method as described for Example 8, but using 2,5-dimethoxyphenacylbromide. The titled compound was isolated as a shite solid (0.33 g, 44.3%) mp 218–220° C.

Example 16
2-[4-(2,6-Dimethoxy-phenyl)-thiazol-2-yl]-1H-benzoimidazole

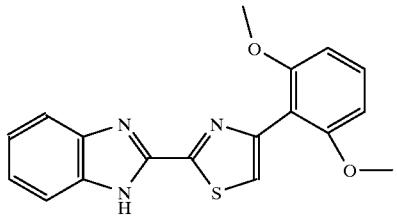

The titled compuond was prepared by the method as described for Example 8, but using 2,6-dimethoxyphenacylbromide. The titled compund was isolated as a dark yellow solid (0.25 g, 36.7%) mp 201.5–203° C.

Example 17
2-[2-(1H-Benzoimidazol-2-yl)-thiazol-4-yl]-phenol

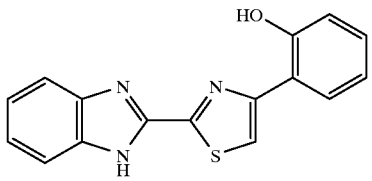

The titled compound was prepared by the method as described for Example 8, but using 2-hydroxyphenacylbromide. The titled compund was isolated as a white solid (2.0 g, 57.6%) mp 239–240.5° C.

Example 18
2-(4-p-Tolyl-thiazol-2-yl)-1H-benzoimidazole

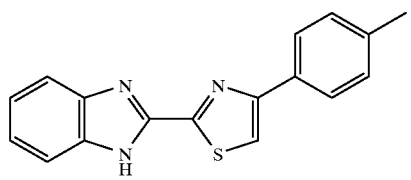

The titled compound was prepared by the method as described for Example 8, but using 4-methylphenacylbromide. The titled compound was isolated as a pale tan solid (0.31 g, 52.0%) mp 232–234° C.

Example 19
2-(4-o-Tolyl-thiazol-2-yl)-1H-benzoimidazole

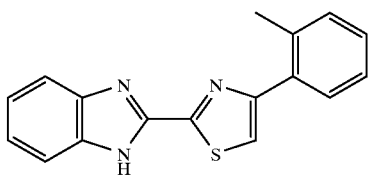

The titled compound was prepared by the method as described for Example 8, but using 2-methylphenacylbromide. The titled compund was isolated as an off white solid (0.14 g, 24.0%) mp 179.9–181° C.

Example 20
2-[4-(3-Chloro-phenyl)-thiazol-2-yl]-1H-benzoimidazole

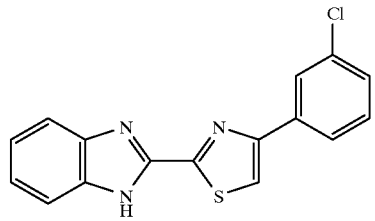

The titled compound was prepared by the method as described for Example 8, but using 3-chlorophenacylbromide. The titled compund was isolated as a yellow needles (0.5 g, 80.0%) mp 238.8–241° C.

Example 21
2-[4-(4-Bromo-phenyl)-thiazol-2-yl]-1H-benzoimidazole

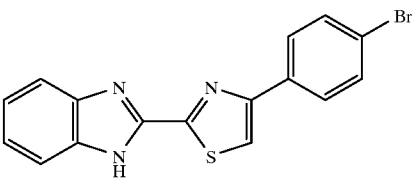

The titled compound was prepared by the method as described for Example 8, but using 4-bromophenacylbromide. The titled compound was isolated as a white solid (0.35 g, 48.0%) mp 253–254.5° C.

Example 22
2-[4-(2,4-Dichloro-phenyl)-thiazol-2-yl]-1H-benzoimidazole

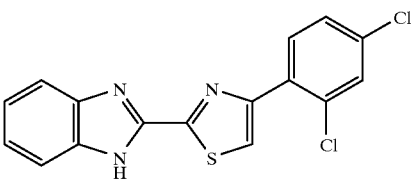

The titled compound was prepared by the method as described for Example 8, but using 2,4-dichlorophenacylbromide. The titled compound was isolated as a yellow solid (0.18 g, 26.0%) mp 227.8–229° C.

Example 23
2-[4-(2-Nitro-phenyl)-thiazol-2-yl]-1H-benzoimidazole

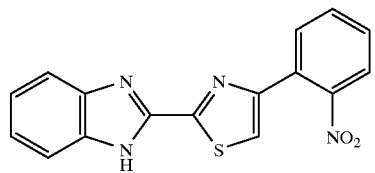

The titled compound was prepared by the method as described for Example 8, but using 2-nitrophenacylbromide. The titled compound was isolated as a yellow solid (0.098 g, 15.2%) mp 204–205.5° C.

Example 24

2-[4-(3-Nitro-phenyl)-thiazol-2-yl]-1H-benzoimidazole

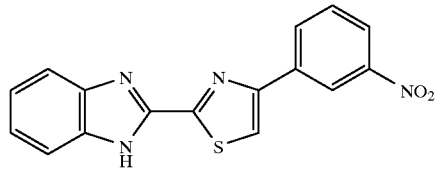

The titled compound was prepared by the method as described for Example 8, but using 3-nitrophenacylbromide. The titled compound was isolated as an off white solid (0.32 g, 51.4%) mp 258–259.5° C.

Example 25

2-[2-(1H-Benzoimidazole-2yl)-thiazol-4-ylmethyl]-isoindole-1,3-dione

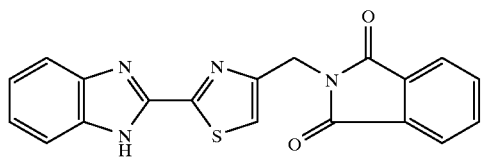

The titled compound was prepared by the method as described for Example 8, but using 1#H/-isoindole-1,3 (2#H/)-dione, 2-(3-bromo-2-oxopropyl)-. The titled compound was isolated as an off white solid (3.0 g, 55.5%) mp 197–199.5° C.

Example 26

2-(5-Phenyl-thiazol-2-yl)-1H-benzoimidazole

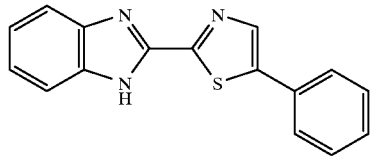

To a solution of phenylacetaldehyde (1.2 g, 10 mmol) in THF (50 ml) was added, with stirring, bromine (1.6 g, 10 mmol) in methylene chloride (5 ml) at 0° C. The reaction mixture was stirred for two hours at room temperature and concentrated. The crude bromide and 1H-Benzoimidazole-2-carbothioic acid amide (0.885 g, 5 mmol) were dissolved in dioxane (50 ml) and refluxed for 3 hours. The solid, separated on cooling, was filtered and washed with water and dimethyl ether. It was then treated with aqueous ammonium hydroxide at 80–90° C. for an hour and filtered while it was hot. The solid was chromatographed using 1:1 ethyl acetate-hexane to isolate 0.44 g of the title compound. mp 186–187° C.

Example 27

2-(5-Bromo-4-phenyl-thiazol-2-yl)-1H-benzoimidazole

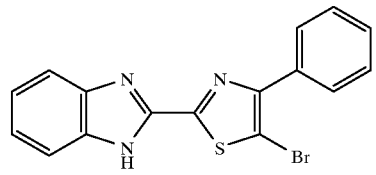

To a solution of 2-(4-Phenyl-thiazol-2-yl)-1H-benzoimidazole (0.5 g, 1.8 mmol) in acetic acid (50 ml), bromine was added at 80° C. The reaction mixture was stirred at 80° C. for overnight. It was then concentrated, diluted with methylene chloride and washed with water, saturated sodium bicarbonate solution and again with water. The organic layer was dried, concentrated and chromatographed (100% methylene chloride) to yield 50 mg (7.8%) of the pure titled compound. mp 207–208° C.

Example 28

2-(1H-Benzoimidazol-2-yl)-4-phenyl-thiazole-5-carboxylic acid ethyl ester

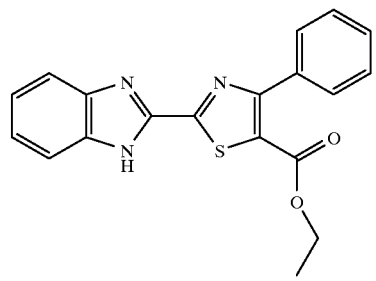

A solution of 1H-Benzoimidazole-2-carbothioic acid amide (2.94 g, 16.6 mmol) 2-bromobenzoylacetic acid ethyl ester (4.5 g, 16.6 mmol) in 3:1 acetic acid-water (100 ml) was refluxed for 3 hours. The reaction mixture was cooled to room temperature and solid was collected. The solid was treated with aqueous sodium bicarbonate. The crude material was chromatographed using THF, and then crystallized from ethyl acetate to yield 1.5 g (25.8%) of the title compound as off white solid. mp 187–188° C.

Example 29

2-(lH-Benzoimidazol-2-yl)-4-phenyl-thiazole-5-carboxylic acid

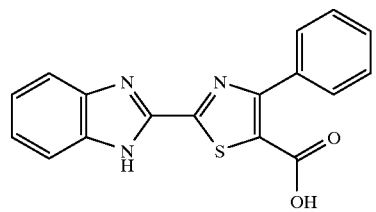

To a solution of 2-(1H-Benzoimidazol-2yl)-4-phenyl-thiazole-5-carboxylic acid ethyl ester (example 28) (1.22 g, 3.5 mmol) in dioxxane (50 ml) was added 1.00 N LiOH (10.25 ml). The reaction mixture was stirred at room temperature for four days and then 3 hours at 50° C. After the reaction was completed, it was concentrated and diluted

Example 30
2-(1H-Benzoimidazol-2-yl)-thhiazole-4-carboxylic acid ethyl ester

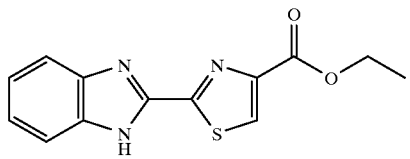

A solution of 1H-Benzoimidazole-2-carbothioic acid amide (2.94 g, 16.6 mmol) 2-bromobenzoylacetic acid ethyl ester (4.5 g, 16.6 mmol) in 3:1 acetic acid-water (100 ml) was refluxed for 3 hours. The reaction mixture was cooled to room temperature and solid was collected. The solid was treated with aqueous sodium bicarbonate. The crude material was chromatographed using THF, and then crystallized from ethyl acetate to yield 1.5 g (25.8%) of the title compound as off white solid. mp 187–188° C.

Example 31
2-(1H-Benzoimidazol-2-yl)-thiazole-4-carboxylic acid

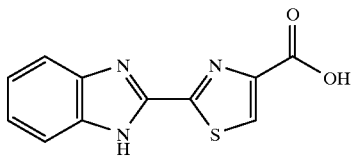

To a solution of 2-(1H-benzoimidazol-2-yl)-thiazole-4-carboxylic acid ethyl ester (Example 30)(2.2 g, 8.0 mmol) in dioxane (550 ml) was added an excess of LiOH and 10 ml of water. The reaction mixture was stirred at room temperature for seven days. After the reaction was completed, it was concentrated and diluted with water (150 ml). It was then extracted with ether and the aqueous layer was acidified with 1N hydrochloric acid. The solid separated was filtered, washed with water and dried in a vacuum oven at 60° C. to yield 1.7 g (86.7%) of the title compund as a light yellow solid. mp>280° C.

Example 32
2-(1H-Benzoimidazol-2-yl)-thiazole-4-carboxylic acid (3-piperidin-1-yl-propyl)-amide

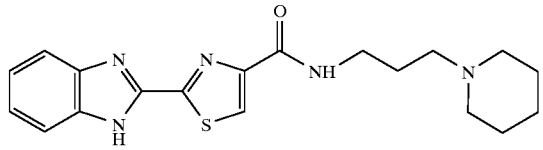

To a mixture of 2-(1H-benzoimidazol-2-yl)-thiazole-4-carboxylic acid (0.123 g 0.5 mmol) and triethylamine (0.061 g, 0.6 mmol) in anhydrous DMF (10 ml) was added isobutylchloroformate (0.075 g, 0.55 mmol) at room temperature. The reaction mixture was stirred for 10 minutes and 1-piperidinepropanamine (0.071 g, 0.5 mmol) was added. The resulting reaction mixture was stirred at room tempera-
ture for 30 minutes. After reaction was completed it was concentrated and iluted with water. It was extracted with ethyl acetate, washed with saturated sodium bicarbonate solution and water, dried and concentrated. The crude material obtained was purified by HPLC (column: NovaPak C-18, solvent system: gradient 1:1 CH$_3$CN-water (1% TFA) to 100% CH$_3$CN to obtain titled compound 0.03 g (10%) as its TFA salt.

Example 33
2-(1H-Benzoimidazol-2-yl)-thiazole-4-carboxylic acid phenylamide

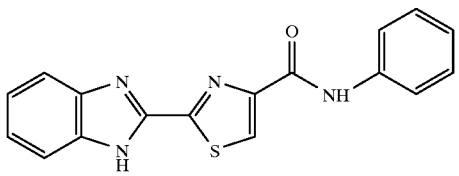

To a mixture of 2-(1H-benzoimidazol-2-yl)-thiazole-4-carboxylic acid (00.123 g 0.5 mmol) and triethylamine (0.061 g, 0.6 mmol) in anhydrous DMF (10 ml) was added isobutylchloroformate (0.075 g, 0.55 mmol) at room temperature. The reaction mixture was stirred for 10 minutes and aniline (0.047 g, 0.5 mmol) was added. The resulting reaciton mixture was stirred at room temperature for 30 minutes. After reaction was completed it was concentrated and diluted with water. It was extracted with ethyl acetate, washed with saturated sodium bicarbonate solution and water, dried and concentrated. The residue obtained from the organic layer was chromatographed using 1:1 ethyl acetate-hexane to yield 0.12 g (75%) of the title compound as a white solid. mp>290° C.

Example 34
[2-(1H-Benzoimidazol-2-yl)-4-phenyl-thiazol-5-yl]-carbamic acid benzyl ester

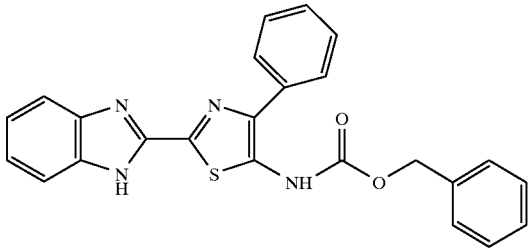

A mixture of 1H-Benzoimidazol-2-carbothioic acid amide (2.94 g, 16.6 mmol) and w-cloro-2-acylamidoacetophenone (3.04 g, 10 mmol) (Drach B. S. et al., Chemistry of Heterocyclic Chemistry, Year 1974, Vol. 10, pages 810–812) in THF was stirred at room temperature and then concentrated. The residue was dissolved in ethyl acetate and was washed with aqueous sodium bicarbonate. The solid obtained from the organic layer was chromatrographed using 10% ethyl acetate in methylene chloride to yield 1.7 g (39.9%) of the title compound as a yellow solid. mp 101–103° C.

Example 35
3-[2-(1H-Benzoimidazol-2-yl)-thiazol-4-yl]-benzonitrile

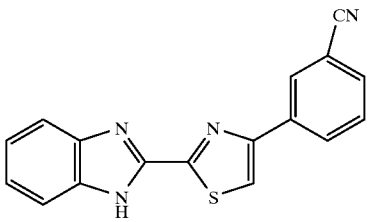

The titled compound was prepared by the method as described for Examle 8, but using 2,4-cyanophenacylbromide. The titled compound was isolated as a light tan solid (0.7 g, 46.3%) mp 258.7–260.5° C.

Example 36
2-(1H-Benzoimidazol-2-yl)-5-phenyl-thiazol-4-ol

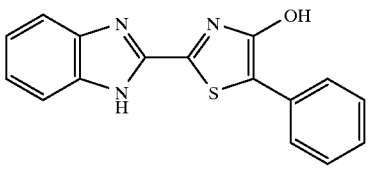

A mixture of 1H-Benzoimidazole-2-carbothioic acid amide (0.885 g, 5 mmol) α-bromophenylacetic acid ethylester (1.54 g, 6.6 mmol) and pyridine (2.0 g, 26.4 mmol) in toluene (50 ml) was heated at 80–90° C. for 3 hours. The reaction mixture was cooled to room temperature and solid Was collected. Crystallization from ethyl alcohol yielded 0.15 gm (10%) of the title compund as an off white crystals. mp>280° C.

Example 37
1-(4-Pyridin-4-yl-thiazol-2-yl)-1H-benzoimidazole

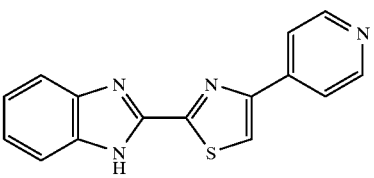

The titled compound was prepared by the method as described for Example 8, but using α-bromo4-acetylpyridine. The titled compound was isolated as a light tan solid (0.7 g, 46.3%) mp 278–280° C.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

We claim:

1. A method for the treatment of inflammatory disease or condition, atherosclerosis or restenosis, in a mammal in need thereof comprising administering to such mammmal an effective amount of a compound of Formula I

FORMULA I

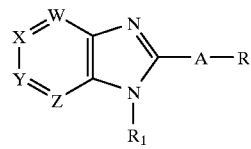

where W, X, Y and Z are each C—H;
$R_1$ is H or lower alkyl of from 1–4 carbon atoms;
wherein A in Formula I is any one of the ring structures recited below wherein the R and the benzimidazole ring are attached to either of the bonds from the ring structures:

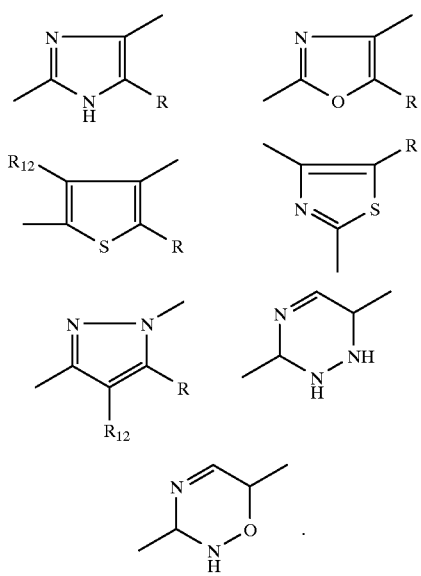

R and $R_{12}$ are independently $R_2$,
cycloalkyl of from 5 to 12 carbon atoms or bicyclic ring structure of from 6 to 12 atoms, either with up to 3 substituents as $R_2$, mono or polyaryl of from 6 to 10 carbon atoms with up to 3 substituents as $R_2$, or
mono or polyheterocyclic of from 5 to 10 atoms having at least one N, O or S atom and up to 3 substituents as $R_2$,
additionally, R and $R_{12}$ when taken together form a mono- or bicyclic ring of from 4 to 10 carbon atoms which is substituted or unsubstituted by an amino group;
$R_2$ is independently
$C_{1-2}$ alkyl,
halogen,
nitro,
$SO_2H$,
—$SO_2$ lower alkyl of from 1–4 carbon atoms,
—$SO_2NR_6R_7$,
alkoxy of from 1–4 carbon atoms;
—$(CH_2)_nNR_6R_7$,
—$N(R_6)C(O)NR_7R_8$,
—$N(R_6)C(S)NR_7R_8$,
—$N(R_6)(CH_2)_nNR_7R_8$
—$(CH_2)_nCONR_6R_7$,
—$(CH_2)_nOR_9$,
—$(CH_2)_nCO_2R_9$,
—$(CH_2)_nOC(O)R_9$, or

—$CF_3$;

n is an integer of from 0 to 4;

$R_6$, $R_7$ and $R_8$ are independently hydrogen, saturated (1–12 carbon atoms) or unsaturated (2–12 carbon atoms) hydrocarbon with terminal functionality of —$NR_9R_{10}$ or nitrogen heterocycle of from 5 to 7 atoms or piperidine with nitrogen or oxygen in position 4 on the ring;

$R_9$ and $R_{10}$ are independently H, alkyl of from 1–4 carbon atoms or benzyl; or a pharmaceutically acceptable salt thereof.

2. The method of claim 1 wherein R or $R_{12}$ may be independently alkyl, unsubstituted mono or polysubstituted cycloalkyl, unsubstituted mono or polysubstituted aryl, unsubstituted mono or polysubstituted heterocyclic, wherein the substitutents may be H, OH, SH, O-alkyl, S-alkyl, halogen, —$NH_2$, dialkylamino, —$NO_2$, or CN.

3. The method of claim 1 wherein $R_1$ is hydrogen.

4. The method of claim 1 wherein A is a thiazolyl ring.

5. The method of claim 1 wherein A in Formula I is any one of the ring structures recited below wherein the R and the benzimidazole ring may be attached to either of the bonds from the ring structures:

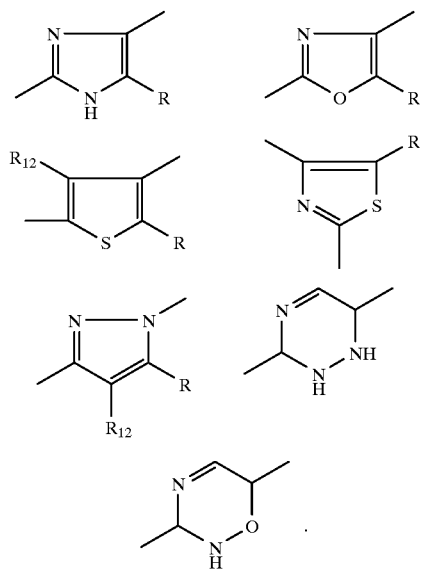

6. The method of claim 1 comprising the compound recited below:

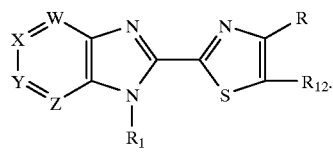

7. The method of claim 1 wherein R may be independently

—$NR_6R_7$,

—$N(R_6)C(O)R_7$,

—$N(R_6)C(O)N(R_7)$ ($R_8$),

—$N(R_6)C(S)N(R_7)$ ($R_8$),

—$N(R_6)$ $(CH_2)_n NR_7R_8$,

—$C(O)NR_7R_8$,

—$OR_6$, or

—$C(O)OR_6$ wherein $R_6$, $R_7$ and $R_8$ can be independently H or saturated or unsaturated hydrocarbon with terminal functionality of

—$NR_9R_{10}$, nitrogen heterocyclic of from 5 to 7 atoms or a piperadine ring with one other N, O or S atom therein.

8. The method of claim 6 wherein $R_1$ is alkyl.

9. The method of claim 6 wherein R contains a pyridyl moiety.

10. The method of claim 6 wherein R contains a benzene ring substituted or unsubstituted.

11. The method of claim 6 wherein R contains a thienyl moiety.

12. The method of claim 6 wherein R contains the moiety —C(O)O.

13. The method of claim 6 wherein R contains an indolyl moiety.

14. The method of claim 1 wherein R contains a pyridyl moiety.

15. The method of claim 1 wherein R contains a benzene ring substituted or unsubstituted.

16. The method of claim 1 wherein R contains a thienyl moiety.

17. The method of claim 1 wherein R contains the moiety —C(O)O.

18. The method of claim 1 wherein R contains an indolyl moiety.

19. The method of claim 1 wherein the compound of Formula I is selected from the group consisting of:

2-[4-(3-Methoxy-phenyl)-thiazol-2-yl]-1H-benzoimidazole;

2-[4-(2-Methoxy-phenyl)-thiazol-2-yl]-1H-benzoimidazole;

2-[4-(4-Methoxy-phenyl)-thiazol-2-yl]-1H-benzoimidazole;

2-(4-Biphenyl-4-yl-thiazol-2-yl)-1H-benzoimidazole;

4-[2-(1H-Benzoimidazol-2-yl)-thiazol-4-yl]-phenol;

4-[2-(1H-Benzoimidazol-2-yl)-thiazol-4-yl]-benzene-1,2-diol;

2-[2-(1H-Benzoimidazol-2-yl)-thiazol-4-yl]-4-bromo-phenol;

2-[4-(2,5-Dimethoxy-phenyl)-thiazol-2-yl]-1H-benzoimidazole;

2-[4-(2,6-Dimethoxy-phenyl)-thiazol-2-yl]-1H-benzoimidazole;

2-[2-(1H-Benzoimidazol-2-yl)-thiazol-4-yl]phenol;

2-(4-p-Tolyl-thiazol-2-yl)-1H-benzoimidazole;

2-(4-O-Tolyl-thiazol-2-yl)-1H-benzoimidazole;

2-[4-(3-Chloro-phenyl)-thiazol-2-yl]-1H-benzoimidazole;

2-[4-(4-Bromo-phenyl)-thiazol-2-yl]-1H-benzoimidizole;

2-[4-(2,4-Dichloro-phenyl)-thiazol-2-yl]-1H-benzoimidazole;

2-[4-(2-Nitro-phenyl)-thiazol-2-yl]-1H-benzoimidazole;

2-[4-(3-Nitro-phenyl)-thiazol-2-yl]-1H-benzoimidazole;

2-[2-(1H-Benzoimidazole-2yl)-thiazol-4-ylmethyl]-isoindole-1,3-dione;

2-(5-Phenyl-thiazol-2-yl)-1H-benzoimidazole;

2-(5-Bromo-4-phenyl-thiazol-2-yl)-1H-benzoimidazole;

2-(1H-Benzoimidazole-2-yl)-4-phenyl-thiazole-5-carboxlic acid ethyl ester;

2-(1H-Benzoimidazol-2-yl)-4-phenyl-thiazole-5-carboxylic acid;
2-(1H-Benzoimidazol-2-yl)-thiazole-4-carbxylic acid ethyl ester;
2-(1H-Benzoimidazol-2-yl)-thiazole-4-carboxylic acid;
2-(1H-Benzoimidazol-2-yl)-thiazole-4-carboxylic acid (3-piperidin-1-yl-propyl)-amide;
2-(1H-Benzoimidazol-2-yl)-thiazole-4-carboxylic acid phenylamide;
[2-(1-H-Benzoimidazol-2-yl)-4-phenyl-thiazol-5-yl]-carbamic acid benzyl ester;
3-[2-(1H-Benzoimidazol-2-yl)-thiazol-4-yl]-benzonitrile;
2-(1H-Benzoimidazol-2-yl)-5-phenyl-thiazol-4-ol; and
1-(4-Pyridin-4-yl-thiazol-2-yl)-1H-benzoimidazole.

20. A method for the treatment of atherosclerosis in a mammal in need thereof comprising administering to such mammal an effective amount of a cornpound of Formula I

FORMULA I

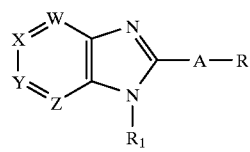

where w, X, Y and Z are each C—H;
$R_1$ is H or lower alkyl of from 1–4 carbon atoms;
wherein A in Formula I is any one of the ring structures recited below wherein the R and the benzimidazole ring are attached to either of the bonds from the ring structures:

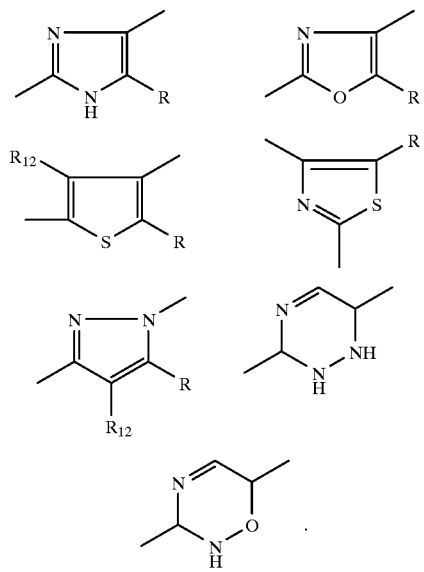

R and $R_{12}$ are independently $R_2$,
cycloalkyl of from 5 to 12 carbon atoms or bicyclic ring structure of from 6 to 12 atoms, either with up to 3 substituents as $R_2$, mono or polyaryl of from 6 to 10 carbon atoms with up to 3 substituents as $R_2$, or mono or polyheterocyclic of from 5 to 10 atoms having at least one N, O or S atom and up to 3 substituents as $R_2$, additionally, R and $R_{12}$ when taken together form a mono- or bicyclic ring of from 4 to 10 carbon atoms which is substituted or unsubstituted by an amino group;
$R_2$ is independently
$C_{1-20}$ alkyl,
halogen,
nitro,
—$SO_2H$,
—$SO_2$ lower alkyl of from 1–4 carbon atoms,
—$SO_2NR_6R_7$,
alkoxy of from 1–4 carbon atoms;
—$(CH_2)_nNR_6R_7$,
—$N(R_6)C(O)NR_7R_8$,
—$N(R_6)C(S)NR_7R_8$,
—$N(R_6)(CH_2)_nNR_7R_8$
—$(CH_2)_nCONR_6R_7$,
—$(CH_2)_nOR_9$,
—$(CH_2)_nCO_2R_9$,
—$(CH_2)_nOC(O)R_9$, or
—$CF_3$;
n is an integer of from 0 to 4;
$R_6$, $R_7$ and $R_8$ are independently hydrogen, saturated (1–12 carbon atoms) or unsaturated (2–12 carbon atoms) hydrocarbon with terminal functionality of —$NR_9R_{10}$ or nitrogen heterocycle of from 5 to 7 atoms or piperidine with nitrogen or oxygen in position 4 on the ring;
$R_9$ and $R_{10}$ are independently H, alkyl of from 1–4 carbon atoms or benzyl; or
a pharmaceutically acceptable salt thereof.

21. A method of treating inflammation in a mammal in need thereof comprising administrating to such mammal an effective anti-inflammatory amount of a compound of Formula I

FORMULA I

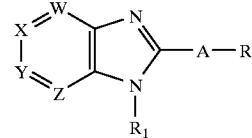

where W, X, Y and Z are each C—H;
$R_1$ is H or lower alkyl of from 1–4 carbon atoms;
wherein A in Formula I is any one of the ring structures recited below wherein the R and the benzimidazole ring are attached to either of the bonds from the ring structures:

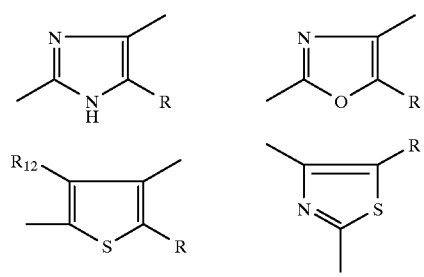

-continued

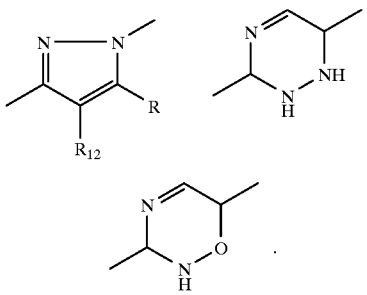

R and R$_{12}$ are independently R$_2$,
cycloalkyl of from 5 to 12 carbon atoms or bicyclic ring structure of from 6 to 12 atoms, either with up to 3 substituents as R$_2$, mono or polyaryl of from 6 to 10 carbon atoms with up to 3 substituents as R$_2$, or
mono or polyheterocyclic of from 5 to 10 atoms having at least one N, O or S atom and up to 3 substituents as R$_2$, additionally, R and R$_{12}$ when taken together from a mono- or bicyclic ring of from 4 to 10 carbon atoms which is substituted or unsubstituted by an amino group;

R$_2$ is independently
C$_{1-20}$ alkyl,
halogen,
nitro,
—SO$_2$H,
—SO$_2$ lower alkyl of from 1–4 carbon atoms,
—SO$_2$NR$_6$R$_7$,
alkoxy of from 1–4 carbon atoms;
(CH$_2$)$_n$NR$_6$R$_7$,
—N(R$_6$)C(O)NR$_7$R$_8$,
—N(R$_6$)C(S)NR$_7$R$_8$,
—N(R$_6$)(CH$_2$)$_n$NR$_7$R$_8$
—(CH$_2$)$_n$OR$_9$,
—(CH$_2$)$_n$CO$_2$R$_9$,
—(CH$_2$)$_n$OC(O)R$_9$, or
—CF$_3$;

n is an integer of from 0 to 4;

R$_6$, R$_7$ and R$_8$ are independently hydrogen, saturated (1–12 carbon atoms) or unsaturated (2–12 carbon atoms) hydrocarbon with terminal functionality of —NR$_9$R$_{10}$ or nitrogen. heterocycle of from 5 to 7 atoms or piperidine with nitrogen or oxygen in position 4 on the ring;

R$_9$ and R$_{10}$ are independently H, alkyl of from 1–4 carbon atoms or benzyli; or a pharmaceutically acceptable salt thereof.

22. A method of inhibiting 15-lipoxygenase in a mammal in need thereof comprising administrating to the mammal an effective inhibiting amount of a compound of Formula I.

FORMULA I

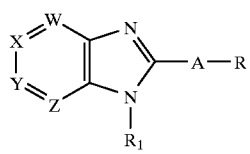

where W, X, Y and Z are each C—H;
R$_1$ is H or lower alkyl of from 1–4 carbon atoms;

wherein A in Formula I is any one of the ring structures recited below wherein the R and the benzimidazole ring are attached to either of the bonds from the ring structures:

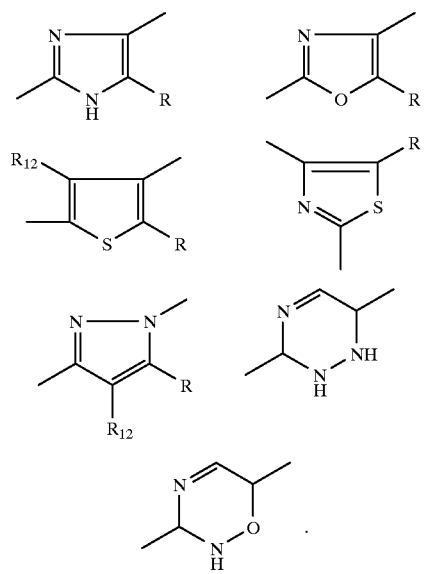

R and R$_{12}$ are independently R$_2$,
cycloalkyl of from 5 to 12 carbon atoms or bicyclic ring structure of from 6 to 12 atoms, either with up to 3 substituents as R$_2$, mono or polyaryl of from 6 to 10 carbon atoms with up to 3 substituents as R$_2$, or
mono or polyheterocyclic of from 5 to 10 atoms having at least one N, O or S atom and up to 3 substituents as R$_2$, additionally, R and R$_{12}$ when taken together form a mono- or bicyclic ring of from 4 to 10 carbon atoms which is substituted or unsubstituted by an amino group;

R$_2$ is independently
C$_{1-20}$ alkyl,
halogen,
nitro,
—SO$_2$H,
—SO$_2$ lower alkyl of from 1–4 carbon atoms,
—SO$_2$NR$_6$R$_7$,
alkoxy of from 1–4 carbon atoms;
—(CH$_2$)$_n$NR$_6$R$_7$,
—N(R$_6$)C(O)NR$_7$R$_8$,
—N(R$_6$)C(S)NR$_7$R$_8$,
—N(R$_6$)(CH$_2$)$_n$NR$_7$R$_8$
—(CH$_2$)$_n$CONR$_6$R$_7$,
—(CH$_2$)$_n$OR$_9$,
—(CH$_2$)$_n$CO$_2$R$_9$,
—(CH$_2$)$_n$OC(O)R$_9$, or
—CF$_3$;

n is an integer of from 0 to 4;

R$_6$, R$_7$ and R$_8$ are independently hydrogen, saturated (1–12 carbon atoms) or unsaturated (2–12 carbon atoms) hydrocarbon with terminal functionality of —NR$_9$R$_{10}$ or nitrogen heterocycle of from 5 to 7 atoms or piperidine with nitrogen or oxygen in position 4 on the ring;

R$_9$ and R$_{10}$ are independently H, alkyl of from 1–4 carbon atoms or benzyl; or a pharmaceutically acceptable salt thereof.

* * * * *

UNITED STATES PATENT AND TRADEMARK OFFICE
CERTIFICATE OF CORRECTION

PATENT NO. : 5,958,950
DATED : Sep. 28, 1999
INVENTOR(S) : Padia et al.

It is certified that error appears in the above-identified patent and that said Letters Patent is hereby corrected as shown below:

Column 22, line 53, "$C_{1-2}$" should read "$C_{1-20}$".

Column 22, line 56, "$SO_2H$" should read "$-SO_2H$".

Column 27, line 38, after "$-N(R_6)(CH_2)_nNR_7R_8$" insert "$-(CH_2)_nCONR_6R_7$".

Column 27, line 51, "benzyli;" should read "benzyl;".

Signed and Sealed this

Twentieth Day of June, 2000

Attest:

Q. TODD DICKINSON

*Attesting Officer*  *Director of Patents and Trademarks*